United States Patent [19]

Skuballa et al.

[11] Patent Number: 4,497,830
[45] Date of Patent: Feb. 5, 1985

[54] CARBACYCLINS, THEIR PREPARATION AND PHARMACOLOGICAL USE

[75] Inventors: Werner Skuballa; Bernd Raduechel; Helmut Vorbrueggen; Jorge Casals-Stenzel; Ekkehard Schillinger; Gerda Mannesmann; Bob Nieuweboer, all of Berlin, Fed. Rep. of Germany

[73] Assignee: Schering Aktiengesellschaft, Berlin and Bergkamen, Fed. Rep. of Germany

[21] Appl. No.: 381,609

[22] Filed: May 24, 1982

[30] Foreign Application Priority Data

May 22, 1981 [DE] Fed. Rep. of Germany ....... 3121155

[51] Int. Cl.³ .................. C07C 33/12; A01K 31/557
[52] U.S. Cl. .................. 514/277; 549/421;
549/475; 556/445; 556/449; 568/648; 568/665;
568/811; 568/819; 514/408; 514/432; 514/438;
514/451; 514/461; 514/517; 514/546;
514/552; 514/573; 514/715; 514/729
[58] Field of Search .............. 560/119; 562/501;
568/819, 811, 648, 665; 556/445, 449; 549/421,
475; 424/339, 343

[56] References Cited

U.S. PATENT DOCUMENTS 4,238,414 12/1980 Morton ................. 564/453
4,306,076 12/1981 Nelson .................. 560/56
4,349,689 9/1982 Aristoff ................ 560/117

FOREIGN PATENT DOCUMENTS 2012265 7/1979 United Kingdom .
2013661 8/1979 United Kingdom ........... 560/119

Primary Examiner—Robert Gerstl
Attorney, Agent, or Firm—Millen & White

[57] ABSTRACT

Compounds of Formula I

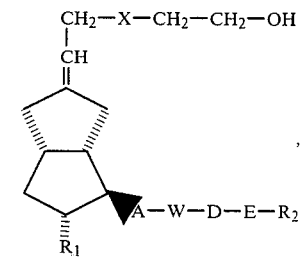

wherein
X is oxygen or $CH_2$;
A is $CH_2-CH_2$, trans-$CH=CH$ or $C\equiv C$;
W is free or functionally modified hydroxymethylene or free or functionally modified

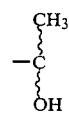

and the OH groups may be in the $\alpha$- or the $\beta$-position;
D is straight chain or branched, saturated or unsaturated hydrocarbon aliphatic of from 1 to 10 carbon atoms, which may be substituted by fluorine;
E is $C\equiv C$ or $CR_3=CR_4$, $R_3$ and $R_4$ being different and being hydrogen or alkyl of 1 to 5 carbon atoms;
$R_1$ is free or functionally modified hydroxy; and
$R_2$ is alkyl, cycloalkyl, optionally substituted aryl or heterocyclic, have valuable pharmacological properties, e.g., hypotensive and bronchodilatory characteristics. They can furthermore be used for prophylaxis and therapy of coronary infarct and as a treatment for stroke. They are produced by means of reduction of the corresponding 1-carbonic acid derivatives.

23 Claims, No Drawings

CARBACYCLINS, THEIR PREPARATION AND PHARMACOLOGICAL USE

BACKGROUND OF THE INVENTION

The present invention relates to new prostacyclin derivatives, a method for producing them and their use as medicines.

In German laid-open applications DE-OS 28 45 770, 29 00 352, 29 02 442, 29 04 655, 29 09 088 and 29 12 409, analogs of (5E)- and (5Z)-6a-carbaprostaglandin I₂ are described. The nomenclature of the compounds of this invention is based on a proposal by Morton and Brokaw (*J. Org. Chem.*, Vol. 44 [1979], p. 2880). In synthesizing these compounds, two double-bond isomers are always created. These are characterized by the symbols (5E) or (5Z). The two isomers of this prototype are illustrated by the following structural formulas:

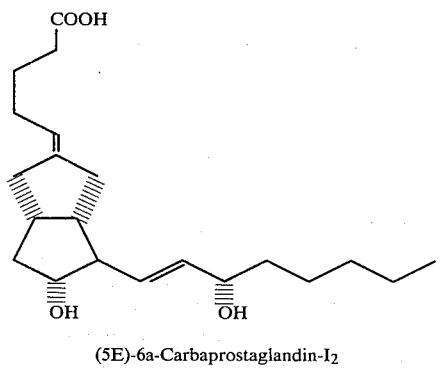

(5E)-6a-Carbaprostaglandin-I₂

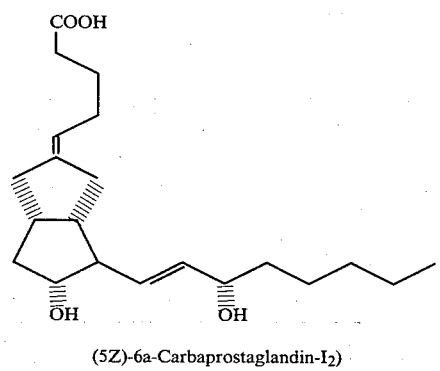

(5Z)-6a-Carbaprostaglandin-I₂)

From the very extensive prior art in prostacyclins and their derivatives, it is known that this class of substances is useful because of their biological and pharmacological properties for treating mammals, including humans. However, their use in medicine frequently meets with difficulties, because the periods of efficacy are too short for therapeutic purposes. All changes in structure in ongoing research have the purpose of both extending the period of efficacy and increasing the selectivity of effectiveness.

SUMMARY OF THE INVENTION

Accordingly, it is an object of this invention to provide such improved prostacyclin compounds.

Upon further study of the specification and appended claims, further objects and advantages of this invention will become apparent to those skilled in the art.

These objects have been achieved by this invention by replacing the 1-carboxyl group in the 6a-carbacyclins and 6a-(3a-oxa)carbacyclins by a hydroxymethyl group, whereby a longer period of efficacy, greater selectivity and improved effectivness is attained.

Thus, this invention relates to carbacyclin derivatives of Formula I:

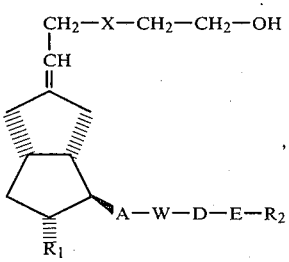

wherein

X is oxygen or $CH_2$;

A is $CH_2-CH_2$, trans—$CH=CH$ or $C\equiv C$;

W is free or functionally modified hydroxymethylene or a free or functionally modified

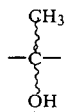

group, wherein the OH groups may be in the α-or the β-position;

D is straight- or branched-chain, optionally unsaturated, alkylene of from 1 to 10 carbon atoms, optionally substituted by fluorine atoms or $C_{1-4}$ alkyl, if the total content of carbon atoms is no more than 10;

E is $C\equiv C$ or $CR_3=CR_4$, wherein $R_3$ and $R_4$ are different and each is hydrogen or alkyl of 1–5 carbon atoms;

$R_1$ is a free or functionally modified hydroxy group; and $R_2$ is alkyl, alkenyl, cycloalkyl, optionally substituted aryl or a heterocyclic group.

The hydroxy groups in $R_1$ and W may be conventionally functionally modified, for instance by conventional etherification or esterification. The free or modified hydroxy groups in W may be in either the α or the β positions, free hydroxy groups being preferred. Suitable ether and acyl groups are well-known to those skilled in the art. Preferred groups are easily cleavable ether radicals, including tetrahydropyranyl, tetrahydrofuranyl, α-ethoxyethyl, trimethylsilyl, dimethyl tertiary-butylsilyl and tribenzylsilyl. Suitable acyl groups can be derived from $C_{1-15}$ hydrocarbon carboxylic or sulfonic acids, e.g., $C_1-C_4$-alkanoyl radicals such as acetyl, propionyl or butyryl or benzoyl.

Suitable groups for $R_2$ include straight- and branched-chain, saturated and unsaturated aliphatic hydrocarbon radicals, preferably saturated, having from 1 to 10 and, in particular, 1 to 7 carbon atoms. These may optionally be substituted by optionally substituted aryl, all defined below for $R_2$ per se. Examples include methyl, ethyl, propyl, butyl, isobutyl, tertiary-butyl, pentyl, hexyl, heptyl, octyl, butenyl, isobutenyl, propenyl, pentenyl, hexenyl, benzyl, and p-chlorobenzyl. Alkyl radicals of 1 to 4 carbon atoms are particularly preferred.

Suitable cycloalkyl groups $R_2$ may contain 4 to 10 and, preferably 5 or 6 carbon atoms in the ring. The rings may be substituted by alkyl groups having from 1 to 4 carbon atoms. Examples include cyclopentyl, cyclohexyl, methylcyclohexyl and adamantyl.

Examples of substituted or unsubstituted $C_{6-10}$-aryl groups $R_2$ or as substituents of the aliphatic groups $R_2$, include; phenyl, 1-naphthyl and 2-naphthyl, which may each be substituted by 1 to 3 halogen atoms, a phenyl group, 1 to 3 alkyl groups each of 1 to 4 carbon atoms, or a chloromethyl, fluoromethyl, trifluoromethyl, carboxyl, $C_1-C_4$-alkoxy or hydroxy group. Preferred is substitution in the 3- or 4-position on the phenyl ring by fluorine, chlorine, $C_1-C_4$-alkoxy or trifluoromethyl, for example, or in the 4-position by hydroxy.

Suitable heterocyclic groups $R_2$ include 5- and 6-member heterocyclics, preferably aromatic, the preferred ones being those having one heteroatom, such as nitrogen, oxygen or sulfur. Examples include 2-furyl, 2-thienyl, 3-thienyl, 2-pyridyl, 3-pyridyl, 4-pyridyl and others.

Suitable alkylene groups D include straight-chain or branched-chain alkylene radicals optionally containing a double bond, but preferably saturated. These have 1 to 10 (together with $C_1-C_4$-alkyl substituents) and, in particular, 1 to 5 carbon atoms. They are optionally substituted by fluorine atoms or $C_1-C_4$-alkyl groups, particularly in the 1- or 2-position. Examples include methylene, flouromethylene, ethylene, 1,2-propylene, ethylethylene, trimethylene, tetramethylene, pentamethylene, 1-methyl-tetramethylene, pentamethylene, 1-methyl-tetramethylene, 1-methyltrimethylene, 2-methyl-trimethylene, 2-methyl-tetramethylene. If a double bond is present, the alkylene radical generally has 4 to 10 carbon atoms, and it exists in the 2- or 3-position.

The alkyl groups $R_3$, $R_4$ and $R_5$ (see below) can be straight chain or branched and have 1 to 5 carbon atoms. Specific examples include the radicals already named for the alkyl $R_2$ groups.

The present invention furthermore relates to a method for producing the carbacyclin derivatives of Formula I comprising, in a manner known per se, reducing a compound of Formula II:

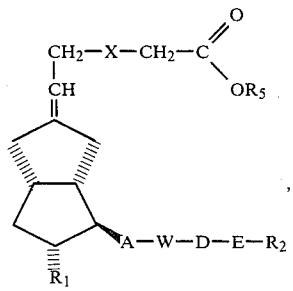

in which $R_1$, $R_2$, X, A, W, D and E are as defined above and $R_5$ is alkyl of 1 to 5 carbon atoms or hydrogen, and, optionally, subsequently separating isomers and/or releasing protected hydroxy groups, in any sequence.

The reduction of the compounds of Formula II can be performed with a conventional reducing agent known to be suitable for the reduction of esters or carbonic acids, such as lithium aluminum hydride, diisobutyl aluminum hydride, and so forth. Suitable solvents include: diethylene ether, tetrahydrofuran, diethylene glycol, dimethyl ether, toluol and so forth. The reduction is performed at temperatures from $-30°$ C. up to the boiling temperature of the solvent used, and preferably from $0°$ C. to $30°$ C.

The release of a functionally modified OH group to produce other compounds of Formula I is also effected by known methods. For example, the splitting of ether protective groups can be performed in an aqueous solution of an organic acid, such as acetic acid, propionic acid and others, or in an aqueous solution of an inorganic acid, such as hydrochloric acid. In order to improve solubility, an inert organic solvent which is miscible with water is advantageously added. Suitable organic solvents include alcohols, such as methanol and ethanol, and ether, such as dimethoxyethane, dioxane and tetrahydrofuran, for example. Tetrahydrofuran is preferred. Splitting is preferably performed at temperatures of $20°$ C. to $80°$ C.

The splitting of silyl ether protective groups is effected, for example, with tetrabutyl ammonium fluoride or with KF in the presence of a crown ether. Examples of suitable solvents include tetrahydrofuran, diethyl ether, dioxane, methylene chloride, etc. The splitting is preferably performed at temperatures of $0°$ C. to $80°$ C.

Many of the starting material compounds of Formula II are known; see, e.g., U.S. Pat. No. 4,238,414, BP's 2,014,143, 2,012,265 and 2,013,661 and U.S. Application Ser. No. 333,099 filed on Dec. 21, 1981, all of whose disclosures are incorporated by reference herein. They can be conventionally produced, by way of example, in a manner known per se, e.g., by converting an aldehyde of Formula III (see, e.g., German laid-open application DE-OS 28 45 770, or its U.S. equivalent Ser. No. 086,506, whose disclosures are incorporated by reference herein)

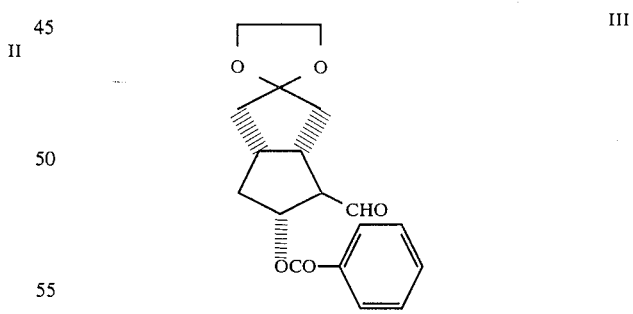

in an olefinizing reaction, with a phosphonate of Formula IV

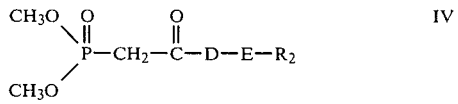

in which D, E and $R_2$ are as defined above, into a ketone of Formula V

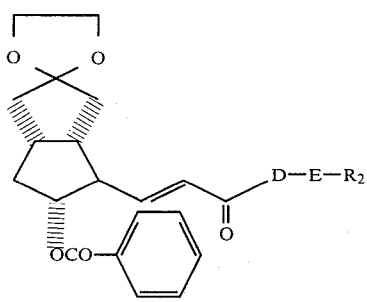

V

After the reduction of the keto group with zinc boron hydride or sodium boron hydride or reaction with alkyl magnesium bromide or alkyl lithium and a subsequent epimer separation and hydrogenation of the double bond or halogenation thereof followed by a double dehydrohalogenation, if needed, compounds of Formula VI are obtained

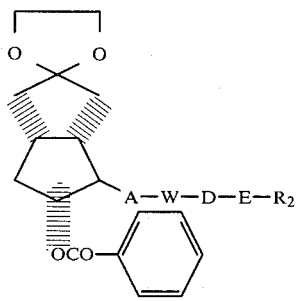

VI

All such reactions and those mentioned below are conventional and discussed, e.g., in the many references cited above.

Saponification of the ester group, for instance with potassium carbonate in methanol, and ketal splitting with aqueous acetic acid, as well as functional modification of the free hydroxy groups, if needed, for instance by etherification with dihydropyran, produces a ketone having Formula VII.

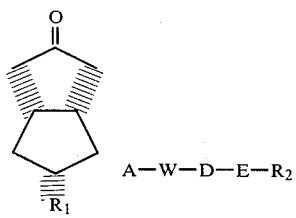

VII

After an olefinizing reaction with phosphonoacetic acid triethyl ester or phosphonoacetic acid trimethyl ester and subsequent reduction with lithium aluminum hydride, the compounds of Formula VIII which are isomeric at the double bonds are obtained; these can be separated as needed.

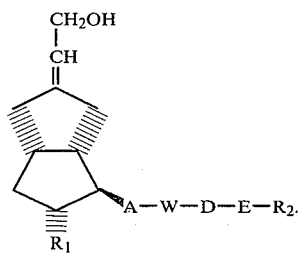

VIII

Etherification of the alcohol VIII with a halogen acetic acid derivative of Formula IX

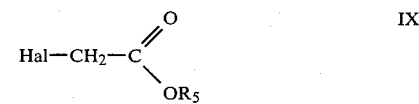

IX in which Hal is a chlorine or bromine atom and $R_5$ is an alkyl radical of 1 to 5 carbon atoms or one hydrogen atom or an alkali metal, in the presence of a base, and a subsequent esterification, as needed, produces the compounds of Formula II, wherein X is oxygen.

The reaction of a compound of Formula VIII with a halogen acetic acid derivative of Formula IX can be performed at temperatures from 0° C. to 100° C., preferably from 10° C. to 80° C., in an aprotic solvent or solvent mixture, such as dimethylsulfoxide, dimethylformamide, tetrahydrofuran, diethylene glycol dimethylether, etc. Suitable bases are those known to one skilled in the art for etherification purposes, such as sodium hydride, potassium tertiary butylate, butyl lithium and so forth.

The starting material compounds of Formula II, wherein X is —$CH_2$— can be produced, for instance, in a manner known per se by reacting a ketone of Formula VII with a Wittig reagent of the Formula X

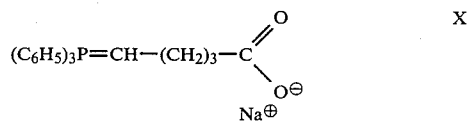

X and, as needed, subsequently separating the double-bond isomers and/or esterifying the free carboxyl group.

The production of the phosphonates of Formula IV is effected in a manner known per se, e.g., by reacting an alkyl halide (produceable from the appropriate alcohol by halogenation) of Formula XI

XI with the diane ion created from the phosphonate of Formula XII

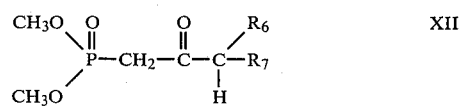

XII in which $R_6$, $R_7$, $R_8$ and $R_9$ are hydrogen, fluorine or an alkyl group of 1 to 5 carbon atoms, and $R_2$ and E are as defined above.

Another means of obtaining the phosphonates of Formula IV involves reacting the anion of methylphosphonic acid dimethyl ester with an ester of Formula XIII

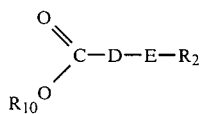     XIII in which D, E and $R_2$ are as defined above and $R_{10}$ is alkyl of 1 to 5 carbon atoms. The latter can be obtained from the appropriate malonic acid ester by alkylation with the halide of Formula XI and subsequent decarbalkoxylation. The ester of Formula XIV

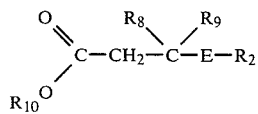     XIV is conventionally obtainable by means of alkylation with the appropriate alkyl halide.

The compounds of this invention reduce blood pressure and act as bronchodilators. They are also suitable for vasodilation, for inhibiting thrombocyte aggregation and for inhibiting the secretion of gastric acid.

The new carbacyclin derivatives of Formula I accordingly, are valuable pharmaceutical agents. Furthermore, with a similar spectrum of effectiveness in comparison with corresponding prostaglandins, they have greater specificity and, above all, a substantially longer-lasting effectiveness. In comparison with $PGI_2$, they are distinguished by greater stability. The high degree of tissue-specificity of the new carbacyclins can be demonstrated by examining smooth-muscle organs such as the guinea pig ileum or the isolated trachea in rabbits, where substantially less stimulation is observed than upon administration of natural prostaglandins of the E-, A- or F-type.

The new carbacyclins have the properties typical of prostacyclins, such as reduction of the peripheral arterial and coronary vascular resistance; inhibition of thrombocyte aggregation and dissolution of platelet thrombi; myocardial cell protection and thus a reduction in systemic blood pressure without at the same time reducing the volume per heartbeat or the efficiency of coronary blood circulation; treatment of heart attack; prophylaxis and therapy in coronary illness, coronary thrombosis, coronary infarct, peripheral artery diseases, arteriosclerosis and thrombosis; therapy for shock; inhibition of bronchoconstriction; inhibition of gastric acid secretion and cell protection for the mucous membranes of the stomach and intestines; anti-allergic properties; reduction in pulmonary vascular resistance and pulmonary blood pressure; promotion of efficient blood circulation in the kidneys; application in place of heparin or as an adjuvant therapy in hemofiltration dialysis, preservation of blood plasma components, in particular blood platelets; inhibition of labor pains and treatment of toxemia during pregnancy; and increasing the efficiency of cerebral blood circulation. The new carbacyclins furthermore have antiproliferative and antidiarrheagenic properties (that is, they prevent accumulations of fluid in the small intestines).

Suitable effective doses of the compounds is 1 to 1500 μg/kg/day, when used in a human patient. The standard unit dose for the pharmaceutically acceptable compositions of this invention is 0.01–100 mg.

When given orally to conscious, hypertonic rats, the compounds of this invention exhibit a greater and longer-lasting effect in reducing blood pressure than $PGE_2$ or $PGA_2$, yet without causing diarrhea as with $PGE_2$ or cardiac arrhythmias as with $PGA_2$.

In anesthetized rabbits, the compounds of this invention exhibit a greater and substantially longer-lasting effect in reducing blood pressure in comparison with $PGE_2$ and $PGA_2$, without affecting other smooth-muscle organs or organ functions.

For parenteral administration, sterile, injectable, aqueous or oil-based solutions are used. For oral application, tablets, lozenges or capsules are suitable examples.

Their administration is analogous to that of $PGI_2$ or other PG-type compounds.

The novel prostacyclin analogs of this invention are substantially more selective with regard to potency, as compared with known PG analogs in causing prostaglandin-like biological responses, and have a substantially longer duration of biological activity. Accordingly, each of these novel prostaglandin analogs is surprisingly and unexpectedly more useful than one of the corresponding conventional prostaglandins for at least one of the pharmacological purposes indicated above because it has a different and narrower spectrum of biological potency than the known prostaglandin, and therefore is more specific in its activity and causes smaller and fewer undesired side effects than when the prostaglandin is used for the same purpose. Moreover, because of its prolonged activity, fewer and smaller doses of the novel prostaglandin analog are frequently effective in attaining the desired result.

The invention thus relates both to medicines per se based on the compounds of Formula I and to conventional auxiliary and carrier substances formulated in combination therewith.

The substances of this invention are intended, e.g., to serve in combination with the conventional auxiliary substances known in the pharmacopeia for the production of agents for reducing blood pressure, for instance.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

(5E)-(16RS)-2-Descarboxy-2-hydroxymethyl-3-oxa-16-methyl-18,18,19,19-tetradehydro-6a-carbaprostaglandin-$I_2$ A solution of 360 mg of (5E)-(16RS)-16-methyl-3-oxa-18,18,19,19-tetradehydro-6a-carba-prostaglandin-$I_2$-methylester-11,15-bis-(tetrahydropyranyl ether) in 25 ml of tetrahydrofuran is added in portions at 0° C. to 180 mg of lithium aluminum hydride and stirred for 30 minutes at 0° C. Excess reagent is then destroyed by the drop-by-drop addition of acetic ester; 3 ml of water is added; the product is stirred for 1 hour, filtered and concentrated by evaporation in a vacuum. The result, in the form of a colorless oil, is 350 mg of (5E)-(16RS)-2-descarboxy-2-hydroxymethyl-3-oxa-16-methyl-18,18,19,19-tetradehydro-6a-carba-prostaglandin-$I_2$-11,15-bis-(tetrahydropyranyl ether).

IR (CHCl$_3$): 3600, 3450, 2942, 2870, 1453, 1440, 972/cm.

In order to split off the protective groups, 320 mg of the bis-tetrahydropyranyl ether is stirred with 30 ml of a mixture of acetic aid, water and tetrahydrofuran (in a proportion of 65:35:10) for 16 hours at room temperature and is then concentrated by evaporation in a vacuum. The residue is chromatographed with methylene chloride/isopropanol (at 9:1) using silica gel. The product obtained is 162 mg of the compound of the above title in the form of a colorless oil.

IR: 3600, 3430, 2999, 2922, 2860, 1600, 1455, 1430, 1105, 971/cm.

The starting material for the above title compound is produced as follows.

1(a)
(5E)-(16RS)-Methyl-3-oxa-18,18,19,19-tetradehydro-6a-carba-prostaglandin-$I_2$-methyl ester-11,15-bis-(tetrahydropyranyl ether)

A solution of 0.5 g of (5E)-(16RS)-methyl-3-oxa-18,18,19,19-tetradehydro-6a-carba-prostaglandin-$I_2$-11,15-bis-(tetrahydropyran-2-yl ether) in 25 ml of methylene chloride is added drop by drop, while stirring at 0° C., to an etheric diazomethane solution until there is a durable yellow coloration. After the solvent is distilled off, the residue is purified by chromatography using silica gel with hexane/ether (at 3:2) and 0.45 g of the title compound is obtained in the form of an oil.

IR: 2945, 2870, 1750, 972/cm.

EXAMPLE 2

(5E)-2-Descarboxy-2-hydroxymethyl-3-oxa-16,16,20-trimethyl-18,18,19,19-tetradehydro-6a-carba-prostaglandin-$I_2$ In analogy to Example 1, 280 mg of the methyl ester produced in accordance with Example 2e yields 268 mg of (5E)-2-descarboxy-2-hydroxymethyl-3-oxa-16,16,20-trimethyl-18,18,19,19-tetradehydro-6a-carba-prostaglandin-$I_2$-11,15-bis-(tetrahydropyranyl ether) in the form of a colorless oil.

IR: 3600, 3430, 2940, 970/cm.

After splitting off the protective groups as in Example 1, 120 mg of the title compound is obtained as a colorless oil.

IR: 3610, 3430, 2925, 2865, 1600, 972/cm.

The starting material for the above title compound is produced as follows.

2(a) 3,3-Dimethyl-2-oxo-oct-5-inyl-phosphonic acid-dimethyl ester

To a suspension of 7.1 g of sodium hydride (50% suspension in oil) in 220 ml of absolute tetrahydrofuran a solution of 31.5 g of 3-methyl-2-oxo-butylphosphonic acid dimethyl ester in 74 ml of absolute tetrahydrofuran is added in drops at 24° C.; the product is stirred for 1.5 hours and then, at 0° C., 111 ml of a 1.6 molar butyl lithium solution in hexane is added drop by drop and stirred for 20 minutes. A solution of 29 g of 1-bromo-2-pentine in 44 ml of absolute tetrahydrofuran is then added to the above solution drop by drop, stirred for 3 hours at 0° C., neutralized with 3N of hydrochloric acid and concentrated in a vacuum. 50 ml of brine is added; extraction is performed three times, each time with 200 ml of methylene chloride; the organic extract is shaken twice, each time with 50 ml of brine; the product is dried with magnesium sulfate and concentrated by evaporation in a vacuum. After distillation of the residue at 0.6 Torr and 125° C., 23 g of the title compound is obtained in the form of a colorless liquid.

IR: 3000, 2962, 2860, 1720/cm.

2(b)
(1R,5S,6R,7R)-3,3-Ethylenedioxy-7-benzoyloxy-6-[(E)-(3R)-3-hydroxy-4,4-dimethyl-non-1-en-6-inyl]-bicyclo[3.3.0]octane.

To a suspension of 0.7 g of sodium hydride (55% suspension in oil) in 60 ml of dimethoxyethane (DME), a solution of 4.5 mg of the phosphonate produced according to Example 2a in 35 ml of DME is added drop by drop at 0° C. and stirred for 1 hour at 0° C. A solution of 4.75 g of (1R,5S,6R,7R)-3,3-ethylenedioxy-7-benzoyloxy-6-formylbicyclo[3.3.0]octane in 60 ml of DME is added at −20° C.; the product is stirred for 1.5 hours at −20° C.; saturated ammonium chloride solution is infused and extraction is performed with ether. The organic extract is washed with neutral water, dried via magnesium sulfate and concentrated in a vacuum. After chromatography of the residue on silica gel, there is obtained with ether/hexane (6:4), 4.7 g of the unsaturated ketone as an oil.

IR: 2940, 2860, 1715, 1670, 1627, 948/cm.

At −40° C., 2.6 g of sodium borohydride is added to a solution of 4.7 g of the ketone and 150 ml of methanol, portion wise, and this is stirred for 1 hour at −40° C. The product is then diluted with ether, washed with neutral water, dried with magnesium sulfate and concentrated in vacuum. By means of column chromatography using silica gel, with ether/hexane (at 7:3), one obtains first 1.8 g of the title compound (PG nomenclature: 15α-hydroxy) and also, as a more-polar component, 1.6 g of the isomeric 15β-hydroxy compound as colorless oils.

IR: 3610, 3410 (wide), 2943, 1712, 1603, 1588, 970, 948/cm.

2(c)
(1R,5S,6R,7R)-7-(Tetrahydropyran-2-yloxy)-6-[(E)-(3R)-4,4-dimethyl-3-(tetrahydropyran-2-yloxy)-non-1-en-6-inyl]-bicyclo[3.3.0]octane-3-one.

A mixture of 1.8 g of the α alcohol produced in accordance with Example 2b and 0.7 grams of potassium carbonate in 60 ml of methanol is stirred for 16 hours at room temperature in argon. The product is then concentrated in a vacuum, diluted with ether and washed with neutral brine. It is dried via magnesium sulfate and concentrated by evaporation in a vacuum. The residue after evaporation is stirred for 16 hours at room temperature with 40 ml of a mixture of acetic acid, water and tetrahydrofuran (at 65:35:10) and then concentrated by evaporation in a vacuum. After filtration of the residue via silica gel, 1.15 g of the ketone is obtained with acetic acid/hexane (at 7:3); the ketone is in the form of an oil.

A solution of 1.15 g of the ketone, 1.2 ml of dihydropyran and 10 mg of p-toluolsulfonic acid in 40 ml of methylene chloride is stirred for 30 minutes at 0° C. The product is then diluted with ether, shaken with dilute sodium bicarbonate solution, washed with neutral water, dried via magnesium sulfate and concentrated by evaporation in a vacuum. 1.65 g of the bis-tetrahydropyranyl ether is obtained, which is used without any further purification.

IR: 2962, 2865, 1738, 972/cm.

2(d)
2-{(E)-(1S,5S,6R,7R)-7-Tetrahydropyran-2-yloxy)-6-[(E)-(3R)-4,4-dimethyl-3-(tetrahydropyran)-2-yloxy)-non-1-en-6-inyl]-bicyclo[3.3.0]octane-3-ylidene}ethane-1-ol At 0° C., 0.9 g of potassium tertiary butylate is added to a solution of 2.1 g of phosphonic acetic acid triethyl ester in 40 ml of tetrahydrofuran, stirred for 10 minutes, mixed with a solution of 2.2 g of the ketone produced according to Example 2c in 20 ml of toluol and stirred at room temperature for 20 hours. The product is diluted with 200 ml of ether, shaken twice with water and once with 20% caustic soda, washed with neutral water, dried via magnesium sulfate and concentrated by evaporation in a vacuum. The residue is filtered with hexane/ether (at 3:2) using silica gel. 1.95 g of the unsaturated ester is obtained in the form of a colorless oil.

IR: 2943, 2865, 1700, 1655, 972/cm.

0.6 g of lithium aluminum hydride is then added in portions at 0° C. to a stirred solution of 1.95 g of the ester produced as above in 60 ml of ether and is stirred for 30 minutes at 0° C. The excess reagent is destroyed by the addition, drop by drop, of acetic ester; 3 ml of water is added and the product is stirred for 2 hours at 20° C., filtered and concentrated by evaporation in a vacuum. The residue is chromatographed with ether/hexane (at 3:2) using silica gel. There is obtained 0.45 g of 2-{(Z)-(1S,5S,6R,7R)-7-(tetrahydropyran-2-yloxy)-6-[(E)-(3R)-4,4-dimethyl-3-(tetrahydropyran-2-yloxy)-non-1-en-6-inyl]-bicyclo[3.3.0]octane-3-ylidene}ethane-1-ol and the less polar compound, 0.7 g of the title compound, in the form of colorless oils.

IR: 3600, 3445, 2940, 2865, 1600, 972/cm.

2(e)
(5E)-3-Oxa-16,16,20-trimethyl-18,18,19,19-tetradehydro-6a-carba-prostaglandin-I$_2$-methyl ester-11,15-bis-(tetrahydropyranyl ether)

To a solution of 830 mg of the alcohol, produced according to Example 2d, in 13 ml of tetrahydrofuran, 170 mg of sodium hydride (a 55% suspension in oil) is added and stirred for 30 minutes at 24° C. A solution of 270 mg of bromoacetic acid in 4.4 ml of tetrahydrofuran is then added drop by drop and the result is heated for 24 hours in reflux. The result is cooled down, acidified with 5% sulfuric acid, subjected to extraction with methylene chloride, shaken with water and concentrated by evaporation in a vacuum. The residue is added to 100 ml of ether and subjected to extraction four times, each time with 20 ml of 4% caustic soda. The alkaline phase is acidified with 5% sulfuric acid and subjected to extraction with methylene chloride; the organic extract is washed three times with water, dried via magnesium sulfate and concentrated by evaporation in a vacuum. The product obtained is 640 mg of the 3-oxa acid as a colorless oil which is uniform in terms of thin-film chromatography and which is converted into the methyl ester in analogy to Example 1a.

IR: 2945, 2865, 1748, 970/cm.

EXAMPLE 3
(5E)-2-Descarboxy-2-hydroxymethyl-3-oxa-16,16-dimethyl-18,18,19,19-tetradehydro-6a-carba-prostaglandin-I$_2$ In analogy to Example 1, 550 mg of the methyl ester produced according to Example 3d yields 540 mg of (5E)-2-descarboxy-2-hydroxy-methyl-3-oxa-16,16-dimethyl-18,18,19,19-tetradehydro-6a-carba-prostaglandin-I$_2$-11,15-bis-(tetrahydropyranyl ether) as a colorless oil.

IR: 3600, 3450, 2942, 2865, 972/cm.

After splitting off the protective groups as in Example 1, 280 mg of the title compound is obtained as a colorless oil.

IR: 3600, 3450, 2926, 2865, 1600, 972/cm.

The starting material for the above title compound is produced as follows.

3(a)
(1R,5S,6R,7R)-3,3-Ethylenedioxy-7-benzoyloxy-6-[(E)-(3R)-3-hydroxy-4,4-dimethyl-oct-1-en-6-inyl]-bicyclo[3.3.0]-octane In analogy to Example 2b, 9.4 g of (1R,5S,6R,7R)-3,3-ethylenedioxy-7-benzoyloxy-6-formyl-bicyclo[3.3.0]-octane and 9.1 g of 3,3-dimethyl-2-oxo-oct-5-inyl-phosphonic acid-dimethyl ester yields 9.2 g of the unsaturated ketone. By means of reduction with sodium boron hydride, 3.7 g of the title compound is obtained in the form of a colorless oil.

IR: 3600, 3400, 2942, 1712, 1602, 1589, 972, 949/cm.

3(b)
(1R,5S,6R,7R)-7-(Tetrahydropyran-2-yloxy)-6-[(E)-(3R)-4,4-dimethyl-3-(tetrahydropyran-2-yloxy)-oct-1-en-6-inyl]-bicyclo[3.3.0]octane-3-one In analogy to Example 2c, 3.7 g of the α alcohol obtained as in Example 3a yields 3.4 g of the bistetrahydropyranyl ether as a colorless oil.

IR: 2960, 2865, 1737, 970/cm.

3(c)
2-{(E)-(1S,5S,6R,7R)-7-(Tetrahydropyran-2-yloxy)-6-[(E)-(3R)-4,4-dimethyl-3-(tetrahydropyran-2-yloxy)-oct-1-en-6-inyl]-bicyclo[3.3.0]octane-3-ylidene}ethane-1-ol In analogy to Example 2d, 3.2 g of the ketone produced as in Example 3b yields 1.1 g of the title compound as a colorless oil.

IR: 3610, 3440, 2942, 2865, 1600, 970/cm.

3(d)
(5E)-16,16-Dimethyl-3-oxa-18,18,19,19-tetradehydro-6a-carba-prostaglandin-I$_2$-methyl ester-11,15-bis(tetrahydropyranyl ether)

In analogy to Example 2e, 1 g of the alcohol produced in accordance with Example 3c yields 760 mg of the title compound as a colorless oil.

IR: 2945, 2865, 1750, 972/cm.

EXAMPLE 4
(5Z)-(16RS)-2-Descarboxy-2-hydroxymethyl-3-oxa-16-methyl-18,18,19,19-tetradehydro-6a-carba-prostaglandin-I$_2$ In analogy to Example 1, 240 mg of (5Z)-(16RS)-16-methyl-3-oxa-18,18,19,19-tetradehydro-6a-carba-prostaglandin-I$_2$-methyl ester-11,15-bis(tetrahydropyranyl ether), produced from the corresponding acid according to Example 1b, yields 240 mg of (5Z)-(16RS)-2-descarboxy-2-hydroxymethyl-3-oxa-16-methyl-18,18,19,19-tetradehydro-6a-carba-prostaglandin-I$_2$-11,15-bis-(tetrahydropyranyl ether) as a colorless oil.

IR: 3610, 3450, 2943, 2865, 1453, 1440, 970/cm.

After splitting off the protective groups as in Example 1, 165 mg of the title compound is obtained as a colorless oil.

IR: 3600, 3435, 2922, 2860, 1600, 1456, 1430, 1105, 970/cm.

EXAMPLE 5

(5E)-(16RS)-2-Descarboxy-16,20-dimethyl-2-hydroxymethyl-3-oxa-18,18,19,19-tetradehydro-6a-carba-prostaglandin-I$_2$ In analogy to Example 1, 340 mg of (5E)-(16RS)-16,20-dimethyl-3-oxa-18,18,19,19-tetradehydro-6a-carba-prostaglandin-I$_2$-methyl ester-11,15-bis-(tetrahydropyranyl ether), produced from the corresponding acid with diazomethane according to Example 1a, yields 335 mg of (5E)-(16RS)-2-descarboxy-16,20-dimethyl-2-hydroxymethyl-3-oxa-18,18,19,19-tetradehydro-6a-carba-prostaglandin-I$_2$-11,15-bis-(tetrahydropyranyl ether) as a colorless oil.

IR: 3600, 3400, 2942, 2870, 972/cm.

After splitting off the protective groups as in Example 1, 145 mg of the title compound are obtained in the form of a colorless oil.

IR: 3610, 3450, 2925, 2860, 1600, 972/cm.

EXAMPLE 6

(5E)-(16RS)-2-Descarboxy-16,20-dimethyl-2-hydroxy methyl-3-oxa-19,19,20,20-tetradehydro-6a-carba-prostaglandin-I$_2$ In analogy to Example 1, 390 mg of (5E)-(16RS)-16,20-dimethyl-3-oxa-19,19,20,20-tetradehydro-6a-carba-prostaglandin-I$_2$-methyl ester-11,15-bis-(tetrahydropyran ether), produced from the corresponding acid with diazomethane as in Example 1a, yields 385 mg of (5E)-(16RS)-2-descarboxy-16,20-dimethyl-2-hydroxymethyl-3-oxa-19,19,20,20-tetradehydro-6a-carba-prostaglandin-I$_2$-11,15-bis-(tetrahydropyranyl ether) as a colorless oil.

IR: 3610, 3450, 2940, 2870, 1602, 974/cm.

After splitting off the protective groups as in Example 1, 220 mg of the title compound are obtained as a colorless oil.

IR: 3610, 3450, 2925, 2962, 1600, 1455, 1432, 1105, 974/cm.

EXAMPLE 7

(5E)-(15RS)-2-Descarboxy-2-hydroxymethyl-15-methyl-3-oxa-18,18,19,19-tetradehydro-6a-carba-prostaglandin-I$_2$ In analogy to Example 1, 180 mg of (5E)-(15RS)-15-methyl-3-oxa-18,18,19,19-tetradehydro-6a-carba-prostaglandin-I$_2$-methyl ester-11,15-bis(tetrahydropyranyl ether), produced from the corresponding acid with diazomethane as in Example 1a, yields 170 mg of (5E)-(15RS)-2-descarboxy-2-hydroxymethyl-15-methyl-3-oxa-18,18,19,19-tetradehydro-6a-carba-prostaglandin-I$_2$-11,15-bis(tetrahydropyranyl ether) as a colorless oil.

IR: 3620, 3440, 2945, 2865, 975/cm.

After splitting off the protective groups as in Example 1, 85 mg of the title compound are obtained as a colorless oil.

IR: 3620, 3450, 2925, 2865, 1602, 975/cm.

EXAMPLE 8

(5E)-2-Descarboxy-2-hydroxymethyl-3-oxa-18,18,19,19-tetradehydro-6a-carba-prostaglandin-I$_2$ In analogy to Example 1, 540 mg of (5E)-3-oxa-18,18,19,19-tetradehydro-6a-carba-prostaglandin-I$_2$-methyl ester-11,15-bis(tetrahydropyranyl ether), produced from the corresponding acid with diazomethane according to Example 1a, yields 530 mg of (5E)-2-descarboxy-2-hydroxymethyl-3-oxa-18,18,19,19-tetradehydro-6a-carba-prostaglandin-I$_2$-11,15-bis-(tetrahydropyranyl ether) as a colorless oil.

IR: 3600, 3420, 2942, 2865, 970/cm.

After splitting off the protective groups as in Example 1, 290 mg of the title compound are obtained as oil.

IR: 3610, 3440, 2925, 2862, 1602, 1455, 1432, 1105, 972/cm.

EXAMPLE 9

(5E)-(16RS)-2-Descarboxy-16,19-dimethyl-2-hydroxymethyl-3-oxa-18,19-didehydro-6a-carba-prostaglandin-I$_2$ In analogy to Example 1, 290 mg of (5E)-(16RS)-16,19-dimethyl-3-oxa-18,19-didehydro-6a-carba-prostaglandin-I$_2$-methyl ester-11,15-bis-(tetrahydropyranyl ether), produced from the corresponding acid as in Example 1, yields 280 mg of (5E)-(16RS)-2-descarboxy-16,19-dimethyl-2-hydroxymethyl-3-oxa-18,19-didehydro-6a-carba-prostaglandin-I$_2$-11,15-bis(tetrahydropyranyl ether) as a colorless oil.

IR: 3600, 3400, 2945, 2865, 974/cm.

After splitting off the protective groups as in Example 1, 155 mg of the title compound are obtained as a colorless oil.

IR: 3600, 3400, 2925, 2865, 1600, 1455, 1435, 1105, 974/cm.

EXAMPLE 10

(5E)-(16RS)-2-Descarboxy-2-hydroxymethyl-16-methyl-18,18,19,19-tetradehydro-6a-carba-prostaglandin-I$_2$ In analogy to Example 1, 400 mg of (5E)-(16RS)-16-methyl-18,18,19,19-tetradehydro-6a-carba-prostaglandin-I$_2$-methyl ester-11,15-bis-(tetrahydropyranyl ether), produced from the corresponding acid with diazomethane as in Example 1a, yields 385 mg of (5E)-(16RS)-2-descarboxy-2-hydroxymethyl-16-methyl-18,18,19,19-tetradehydro-6a-carba-prostaglandin-I$_2$-11,15-bis-(tetrahydropyranyl ether) as a colorless oil.

IR: 3610, 3450, 2945, 2865, 974/cm.

After splitting off the protective groups as in Example 1, 235 mg of the title compound are obtained as a colorless oil.

IR: 3600, 3400, 2925, 2865, 1600, 974/cm.

EXAMPLE 11

(5E)-2-Descarboxy-2-hydroxymethyl-16,16-20-trimethyl-18,18,19,19-tetradehydro-6a-carba-prostaglandin-I$_2$ In analogy to Example 1, 550 mg of the methyl ester produced according to Example 11a yields 540 mg of (5E)-2-descarboxy-2-hydroxymethyl-16,16,20-trimethyl-18,18,19,19-tetradehydro-6a-carba-prostaglandin-$I_2$-11,15-bis-(tetrahydropyranyl ether) as a colorless oil.

IR: 3600, 3420, 2940, 2865, 972/cm.

After splitting off the protective groups as in Example 1, 325 mg of the title compound are obtained as a colorless oil.

IR: 3600, 3400, 2925, 2865, 1600, 972/cm.

The starting material for the above title compound is produced as follows.

11(a)

(5E)-16,16,20-Trimethyl-18,18,19,19-tetradehydro-6a-carba-prostaglandin-$I_2$-methyl ester-11,15-bis-(tetrahydropyranyl ether)

To a solution of 15 g of 4-carboxybutyltriphenylphosphonium bromide in 35 ml of absolute dimethyl sulfoxide (DMSO), at 15° C. in argon, 60 ml of a 1.04 molar solution of methylsulfinyl methyl sodium in DMSO is added drop by drop and stirred for 30 minutes at 20° C. To the red ylene solution, a solution of 2.5 g of the ketone produced according to Example 2c in 15 ml of absolute DMSO is added drop by drop, and the result is stirred for 5 hours at 45° C. The reaction mixture is poured onto ice water, acidified with 10% citric acid solution to pH 4–5 and subjected to extraction three times with methylene chloride. The organic phase is shaken with brine, dried via magnesium sulfate and concentrated by evaporation in a vacuum. After chromatography of the residue using silica gel, the result first obtained, with ether/hexane (at 1:1), is 0.7 g of (5Z)-16,16,20-trimethyl-18,18,19,19-tetradehydro-6a-carba-prostaglandin-$I_2$-11,15-bis-(tetrahydropyran-2-yl ether), as well as the more-polar component, 1.2 g of (5Z)-16,16,20-trimethyl-18,18,19,19-tetradehyro-6a-carba-prostaglandin-$I_2$-11,15-bis-(tetrahydropyranyl ether), in the form of colorless oils.

IR: 3510 (wide), 2960, 2868, 1710, 974/cm.

For the purpose of esterification, 1.2 g of the above-obtained (E)-configuration acid is dissolved in 60 ml of methylene chloride and mixed at 0° C., drop by drop, with an etheric diazomethane solution until there is a durable yellow coloration. After evaporation of the solvent, the residue is purified by chromatography with silica gel and hexane/ether (at 3:2), yielding 1.1 g of the title compound as an oil.

IR: 1735, 875/cm.

EXAMPLE 12

(5E)-2-Descarboxy-16,16-dimethyl-2-hydroxymethyl-18,18,19,19-tetradehydro-6a-carba-prostaglandin-$I_2$ In analogy to Example 1, 320 mg of the methyl ester produced according to Example 12a yields 305 mg of (5E)-2-descarboxy-16,16-dimethyl-2-hydroxymethyl-18,18,19,19-tetradehydro-6a-carba-prostaglandin-$I_2$-11,15-bis-(tetrahydropyranyl ether) as a colorless oil.

IR: 3610, 3400, 2942, 2866, 974/cm.

After splitting off the protective groups as in Example 1, 170 mg of the title compound are obtained as an oil.

IR: 3600, 3450, 2928, 2865, 1602, 974/cm.

The starting material for the above title compound is produced as follows.

12(a)

(5E)-16,16-Dimethyl-18,18,19,19-tetradehydro-6a-carba-prostaglandin-$I_2$-methyl ester-11,15-bis-(tetrahydropyranyl ether)

In analogy to Example 11a, 2.8 g of the ketone produced according to Example 3b yields 1.35 g of (5E)-16,16-dimethyl-18,18,19,19-tetradehydro-6a-carba-prostaglandin-$I_2$-11,15-bis-(tetrahydropyranyl ether) as a colorless oil.

IR: 3500 (wide), 2962, 2870, 1712, 975/cm.

By esterification of the above-obtained acid with etheric diazomethane solution according to Example 11a, 1.2 g of the title compound are obtained as an oil.

IR: 1736, 975/cm.

EXAMPLE 13

(5E)-(16RS)-2-Descarboxy-16,20-dimethyl-2-hydroxymethyl-18,18,19,19-tetradehydro-6a-carba-prostaglandin-$I_2$ In analogy to Example 1, 420 mg of (5E)-(16RS)-16,20-dimethyl-18,18,19,19-tetradehydro-6a-carba-prostaglandin-$I_2$-methyl ester-11,15-bis-(tetrahydropyranyl ether), produced from the corresponding acid with diazomethane as in Example 1, yields 400 mg of (5E)-(16RS)-2-descarboxy-16,20-dimethyl-2-hydroxymethyl-18,18,19,19-tetradehydro-6a-carba-prostaglandin-$I_2$-11,15-bis-(tetrahydropyranyl ether) as a colorless oil.

IR: 3610, 3450, 2945, 2865, 975/cm.

After splitting off the protective groups as in Example 1, 270 mg of the title compound are obtained as an oil.

IR: 3600, 3400, 2930, 2860, 1602, 975/cm.

EXAMPLE 14

(5E)-(16RS)-2-Descarboxy-16,20-dimethyl-2-hydroxymethyl-19,19,20,20-tetradehydro-6a-carba-prostaglandin-$I_2$ In analogy to Example 1, 400 mg of (5E)-(16RS)-16,20-dimethyl-19,19,20,20-tetradehydro-6a-carba-prostaglandin-$I_2$-methyl ester-11,15-bis-(tetrahydropyranyl ether), produced from the corresponding acid with diazomethane as in Example 1, yields 370 mg of (5E)-(16RS)-2-descarboxy-16,20-dimethyl-2-hydroxymethyl-19,19,20,20-tetradehydro-6a-carba-prostaglandin-$I_2$-11,15-bis-(tetrahydropyranyl ether) as a colorless oil.

IR: 3600, 3450, 2950, 2862, 976/cm.

The splitting off of the protective groups is effected in analogy to Example 1. 200 mg of the title compound are obtained as an oil.

IR: 3600, 3420, 2944, 2860, 1600, 976/cm.

EXAMPLE 15

(5E)-(15RS)-2-Descarboxy-2-hydroxymethyl-15-methyl-18,18,19,19-tetradehydro-6a-carba-prostaglandin-$I_2$ In analogy to Example 1, 200 mg of (5E)-(15RS)-15-methyl-18,18,19,19-tetradehydro-6a-carba-prostaglandin-$I_2$-methyl ester-11,15-bis-(tetrahydropyranyl ether), produced from the corresponding acid with diazomethane as in Example 1, yields 150 mg of (5E)-(15RS)-2-descarboxy-2-hydroxymethyl-15-methyl-18,18,19,19-tetrahydro-6a-carba-prostaglandin-$I_2$-11,15-bis-(tetrahydropyranyl ether) as an oil.

IR: 3600, 3452, 2952, 2860, 978/cm.

The splitting off of the protective groups is effected analogously to Example 1. 85 mg of the title compound are obtained as an oil.

IR: 3605, 3420, 2948, 2862, 1600, 978/cm.

EXAMPLE 16

(5E)-2-Descarboxy-2-hydroxymethyl-18,18,19,19-tetradehydro-6a-carba-prostaglandin-$I_2$ In analogy to Example 1, 400 mg of (5E)-18,18,19,19-tetradehydro-6a-carba-prostaglandin-$I_2$-methyl ester-11,15-bis-(tetrahydropyranyl ether), produced from the corresponding acid and diazomethane as in Example 1, yields 365 mg of (5E)-2-descarboxy-2-hydroxymethyl-18,18,19,19-tetradehydro-6a-carb-prostaglandin-$I_2$-11,15-bis-(tetrahydropyranyl ether) as oil.

IR: 3620, 3450, 2952, 2866, 978/cm.

Splitting off of the protective groups is done analogously to Example 1. The result is 185 mg of the title compound as an oil.

IR: 3600, 3425, 2948, 2860, 978/cm.

EXAMPLE 17

(5E)-(16RS)-2-Descarboxy-16,19-dimethyl-18,19-didehydro-2-hydroxymethyl-6a-carba-prostaglandin-$I_2$ In analogy to Example 1, 500 mg of (5E)-(16RS)-16,19-dimethyl-18,19-didehydro-6a-carba-prostaglandin-$I_2$-methyl ester-11,15-bis-(tetrahydropyranyl ether), produced from the corresponding acid with diazomethane as in Example 1, yields 430 mg of (5E)-(16RS)-2-descarboxy-16,19-dimethyl-18,19-didehydro-2-hydroxymethyl-6a-carba-prostaglandin-$I_2$-11,15-bis-(tetrahydropyranyl ether) as an oil.

IR: 3610, 3452, 2950, 2864, 980/cm.

Splitting off of the protective groups is effected as in Example 1. The result is 250 mg of the title compound as an oil.

IR: 3600, 3420, 2946, 2858, 1602, 978/cm.

The preceding examples can be repeated with similar success by substituting the generically or specifically described reactants and/or operating conditions of this invention for those used in the preceding examples. From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of the formula

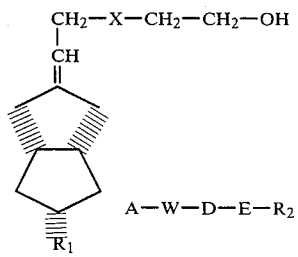

wherein
X is oxygen or —$CH_2$—;
A is $CH_2$—$CH_2$, trans—CH=CH— or C≡C—;
W is -CH(OR)-or

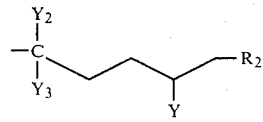

wherein in the latter group OR may be in the α- or β-position;

-D-E-$R_2$ has the structure

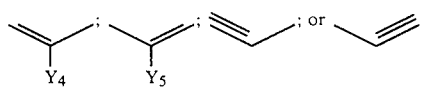

wherein $Y_2$ and $Y_3$ are independently each H or $C_{1-4}$-alkyl and

represents

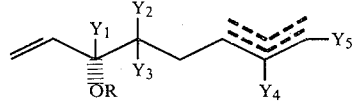

wherein $Y_4$ is $C_{1-5}$-alkyl; and $Y_5$ is H or $C_{1-5}$-alkyl and is different from $R_2$;

$R_1$ is OR;

$R_2$ is H; $C_{1-10}$-alkyl; $C_{1-10}$-alkenyl; $C_{1-10}$-alkyl or $C_{1-10}$-alkenyl, each substituted by $C_{4-10}$-aryl or substituted $C_{4-10}$-aryl as defined below; $C_{4-10}$-cycloalkyl; $C_{4-10}$-cycloalkyl substituted by $C_{1-4}$-alkyl; $C_{4-10}$-aryl; $C_{4-10}$-aryl substituted by 1 to 3 halogen atoms, a phenyl group, 1 to 3 alkyl groups each of 1 to 4 carbon atoms, or a chloromethyl, fluoromethyl, trifluoromethyl, carboxyl, $C_1$–$C_4$-alkoxy or hydroxy group; or an aromatic heterocycle or 5 or 6 ring atoms, one of which is O, N or S, the remainder being carbon atoms; and R is H or tetrahydropyranyl, tetrahydrofuranyl, α-ethoxyethyl, trimethylsilyl, dimethyl-tert-butylsilyl, tribenzylsilyl or an acyl group of a $C_{1-15}$-hydrocarbon carboxylic or sulfonic acid.

2. A compound of claim 1, wherein A-W-D-E-$R_2$ has the structure

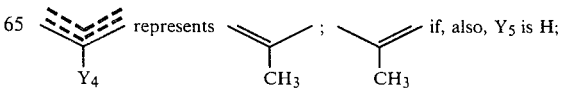

wherein $Y_1$, $Y_2$, $Y_3$ and $Y_5$ are independently each H or $CH_3$ and

-continued

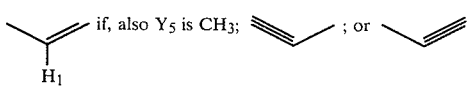

3. A compound of claim 1 or 2, wherein E is —C≡C—.

4. (5E)-(16RS)-2-Descarboxy-2-hydroxymethyl-3-oxa-16-methyl-18,18,19,19-tetradehydro-6a-carba-prostaglandin-I$_2$, a compound of claim 1.

5. (5E)-2-Descarboxy-2-hydroxymethyl-3-oxa-16,16,20-trimethyl-18,18,19,19-tetradehydro-6a-carba-prostaglandin-I$_2$, a compound of claim 1.

6. (5E)-2-Descarboxy-2-hydroxymethyl-3-oxa-16,16-dimethyl-18,18,19,19-tetradehydro-6a-carba-prostaglandin-I$_2$, a compound of claim 1.

7. (5Z)-(16RS)-2-Descarboxy-2-hydroxymethyl-3-oxa-16-methyl-18,18,19,19-tetradehydro-6a-carba-prostaglandin-I$_2$, a compound of claim 1.

8. (5E)-(16RS)-2-Descarboxy-16,20-dimethyl-2-hydroxymethyl-3-oxa-18,18,19,19-tetradehydro-6a-carba-prostaglandin-I$_2$, a compound of claim 1.

9. (5E)-(16RS)-2-Descarboxy-16,20-dimethyl-2-hydroxymethyl-3-oxa-19,19,20,20-tetradehydro-6a-carba-prostaglandin-I$_2$, a compound of claim 1.

10. (5E)-(15RS)-2-Descarboxy-2-hydroxymethyl-15-methyl-3-oxa-18,18,19,19-tetradehydro-6a-carba-prostaglandin-I$_2$, a compound of claim 1.

11. (5E)-2-Descarboxy-2-hydroxymethyl-3-oxa-18,18,19,19-tetradehydro-6a-carba-prostaglandin-I$_2$, a compound of claim 1.

12. (5E)-(16RS)-2-Descarboxy-16,19-dimethyl-2-hydroxymethyl-3-oxa-18,19-didehydro-6a-carba-prostaglandin-I$_2$, a compound of claim 1.

13. (5E)-(16RS)-2-Descarboxy-2-hydroxymethyl-16-methyl-18,18,19,19-tetradehydro-6a-carba-prostaglandin-I$_2$, a compound of claim 1.

14. (5E)-2-Descarboxy-2-hydroxymethyl-16,16-20-trimethyl-18,18,19,19-tetradehydro-6a-carba-prostaglandin-I$_2$, a compound of claim 1.

15. (5E)-2-Descarboxy-16,16-dimethyl-2-hydroxymethyl-18,18,19,19-tetradehydro-6a-carba-prostaglandin-I$_2$, a compound of claim 1.

16. (5E)-(16RS)-2-Descarboxy-16,20-dimethyl-2-hydroxymethyl-18,18,19,19-tetradehydro-6a-carba-prostaglandin-I$_2$, a compound of claim 1.

17. (5E)-(16RS)-2-Descarboxy-16,20-dimethyl-2-hydroxymethyl-19,19,20,20-tetradehydro-6a-carba-prostaglandin-I$_2$, a compound of claim 1.

18. (5E)-(15RS)-2-Descarboxy-2-hydroxymethyl-15-methyl-18,18,19,19-tetradehydro-6a-carba-prostaglandin-I$_2$, a compound of claim 1.

19. (5E)-2-Descarboxy-2-hydroxymethyl-18,18,19,19-tetradehydro-6a-carba-prostaglandin-I$_2$, a compound of claim 1.

20. (5E)-(16RS)-2-Descarboxy-16,19-dimethyl-18,19-didehydro-2-hydroxymethyl-6a-carba-prostaglandin-I$_2$, a compound of claim 1.

21. A pharmaceutical composition comprising an amount of a compound of claim 1 effective to lower blood pressure and a pharmaceutically acceptable carrier.

22. A composition of claim 21 containing more than one pharmacologically active compound.

23. A method of lowering blood pressure in a patient in need of such treatment comprising administering to the patient an amount of a compound of claim 1 effective to lower blood pressure.

* * * * *